(12) United States Patent
Padron et al.

(10) Patent No.: US 7,890,346 B2
(45) Date of Patent: *Feb. 15, 2011

(54) HEALTH SERVICES DELIVERY SYSTEM WITH INCENTIVES

(76) Inventors: Nicanor Padron, 11800 SW. 18 St. #108, Miami, FL (US) 33175; Jose Julian Padron, 11800 SW. 18 St. #108, Miami, FL (US) 33175

(*) Notice: Subject to any disclaimer, the term of this patent is extended or adjusted under 35 U.S.C. 154(b) by 0 days.

This patent is subject to a terminal disclaimer.

(21) Appl. No.: 12/657,142

(22) Filed: Jan. 13, 2010

(65) Prior Publication Data

US 2010/0161349 A1 Jun. 24, 2010

Related U.S. Application Data

(63) Continuation of application No. 11/098,760, filed on Apr. 4, 2005, now Pat. No. 7,672,857, which is a continuation-in-part of application No. 10/340,929, filed on Jan. 13, 2003, now abandoned, which is a continuation-in-part of application No. 09/603,529, filed on Jun. 23, 2000, now abandoned.

(51) Int. Cl.
*G06Q 10/00* (2006.01)
*G06Q 50/00* (2006.01)

(52) U.S. Cl. .................. 705/2; 705/3; 705/4; 600/300; 707/100

(58) Field of Classification Search .................. 707/100
See application file for complete search history.

(56) References Cited

U.S. PATENT DOCUMENTS

| | | | |
|---|---|---|---|
| 5,233,514 A * | 8/1993 | Ayyoubi et al. .......... 705/14.26 |
| 5,301,105 A | 4/1994 | Cummings, Jr. | |
| 5,692,501 A * | 12/1997 | Minturn ..................... 600/301 |
| 6,039,688 A | 3/2000 | Douglas et al. | |
| 6,161,096 A | 12/2000 | Bell | |
| 6,351,738 B1 | 2/2002 | Clark | |
| 2002/0029177 A1 | 3/2002 | Smisek | |

OTHER PUBLICATIONS

Caldwell (Caldwell, Bernice. Employee Benefit Plan Review. New York: May 1992. vol. 46, Is. 11; p. 50.*
Caldwell, Bernice, Employee Benefit Plan Review, New York: May 1992, vol. 46, Is. 11; p. 50.

(Continued)

*Primary Examiner*—Linh-Giang Michelle Le
(74) *Attorney, Agent, or Firm*—Greenberg Traurig, P.A.

(57) ABSTRACT

A system of health care service and an associated method of the administration thereof to a plurality of subscribers including a providing entity organizationally structured to implement a health care program which includes categorizing subscribers desirous of health care service, including preventative services, into a plurality of predetermined profiles. The profiles are defined by personal characteristics including age, gender, clinical history, etc. and each profile is associated with a predetermined curative or preventative treatment regimen with which a respective subscriber is expected to comply. An incentive system is implemented to motivate the subscribers into compliance with the assigned treatment regimen and comprises the assignment of credits and penalties based on a degree of compliance with the treatment regimen. Valuable consideration is awarded to the subscriber evidencing a satisfactory degree of compliance.

9 Claims, 4 Drawing Sheets

OTHER PUBLICATIONS

Newman, Barry, "Penalties, incentives & wellness programs after HIPAA," Employee Benefits Journal, Mar. 1999, pp. 29-32.

Sarah D. Stanwick, et al., How wellness programs can boost the bottom line through employee involvement—The Journal of Corporate Accounting & Finance, vol. 10, Issue 4, Summer.

Questions & Answers, Employee Benefits Plan Review, vol. 49, Issue 12, Jun. 1995, p. 8.

Stephanie Armour, Employer benefit survey targets unhealthy habits, USA Today, May 28, 1998, p. 01B.

* cited by examiner

HEALTH SERVICES DELIVERY SYSTEM WITH INCENTIVES

CLAIM OF PRIORITY/CONTINUITY INFORMATION

The present application is a continuation application of pending U.S. nonprovisional application Ser. No. 11/098,760 filed on Apr. 4, 2005, which in turn is a continuation-in-part application of application Ser. No. 10/340,929 filed on Jan. 13, 2003, which in turn is a continuation-in-part application of application Ser. No. 09/603,529 filed on Jun. 23, 2000. All of said applications are incorporated herein by reference in their entireties. The benefit of the earlier filing date of each of said applications is claimed pursuant to 35 U.S.C. Section 120.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office Patent file or records, but otherwise reserves all copyright rights whatsoever.

BACKGROUND OF THE INVENTION

1. Field of the Invention

The present invention is directed to a health care system and a method for the administration thereof by a providing entity, wherein a plurality of subscribers desirous of health care service are profiled according to personal characteristics and assigned a treatment regimen dependent on medical needs, preferably even before they exhibit a need for any health care services. A motivating incentive system is implemented to facilitate compliance with the assigned treatment regimen and involves the assignment of both credits and penalties to the subscriber based on the degree of compliance with the corresponding treatment regimen. Motivational awards are provided to the subscriber evidencing a satisfactory compliance with the assigned treatment regimen and ensuring in the best possible manner the effectiveness of preventative, family and community medicine plans.

2. Description of the Related Art

Many business and operational arrangements have been designed in the past for delivering health services to subscribers. Health maintenance organizations have been created with different philosophies to accomplish this at a minimum cost. However, systems that include incentives to their subscribers constitute a minority. None of them, however, include a system that issues credits as equity units in the use of the system when a subscriber complies with a sequence of events associated with the profile and/or treatment regimen in which he/she has been classified.

One of these incentive systems is described in U.S. Pat. No. 5,806,045 issued to Biorge et al. in 1998, and directed to a method and system for allocating and redeeming incentive credits between a portable device and a base device. This system is typical in that it accumulates credits that can be redeemed in subsequent transactions. However, the system and method of this patent is absent the classification of subscribers or users under a particular profile that requires them to perform certain acts for the incentives to be awarded, as it is the case in the present invention, as will be described hereinafter.

Applicant believes that another of these systems is disclosed in U.S. Pat. No. 5,301,105 issued to Cummings, Jr. in Apr. 5, 1994 for All Care Health Management System. The Cumming's system describes a fully integrated health care system and its interaction of the patient, health care provider, financially institution, etc. However, Cumming's system differs in many ways from the present invention including, but not limited to, a failure to issue credits as equity units or interests in the providing entity or the awarding of penalties to the participants.

Other patents describing the closest subject matter provide for a number of more or less complicated features that fail to solve the problem in an efficient and economical way. None of these patents suggest the novel features of the present invention, which, among other benefits, involves all of the subscribers, in the system of incentives and penalties, and in addition to providing health benefits according to the subscriber's medical profile, provides a parallel for capitalization that is created with the economic funds assigned for the implementation of the incentives and penalties system, enabling in some instances a loan company to participate in the health services by mutual agreement and as permitted by law and other regulations.

SUMMARY OF THE INVENTION

It is one of the main objects of the present invention to provide a system and method for providing and administering health services to a number of subscribers at minimum cost while enhancing their health.

It is another object of this invention to provide a system and method that permits the user to selectively provide incentives to those subscribers who participate in a number of predetermined prescribed activities intended to improve their health or prevent more serious health consequences, without requiring the enrolled patient to suffer from a specific ailment in order to initiate the treatment.

It is still another object of the present invention to provide a system and method of implementation that is inexpensive and effective.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention comprises details which will be more fully understood from the following description, when read in conjunction with the accompanying drawings in which.

DETAILED DESCRIPTION OF THE PREFERRED EMBODIMENT

Figure 1:
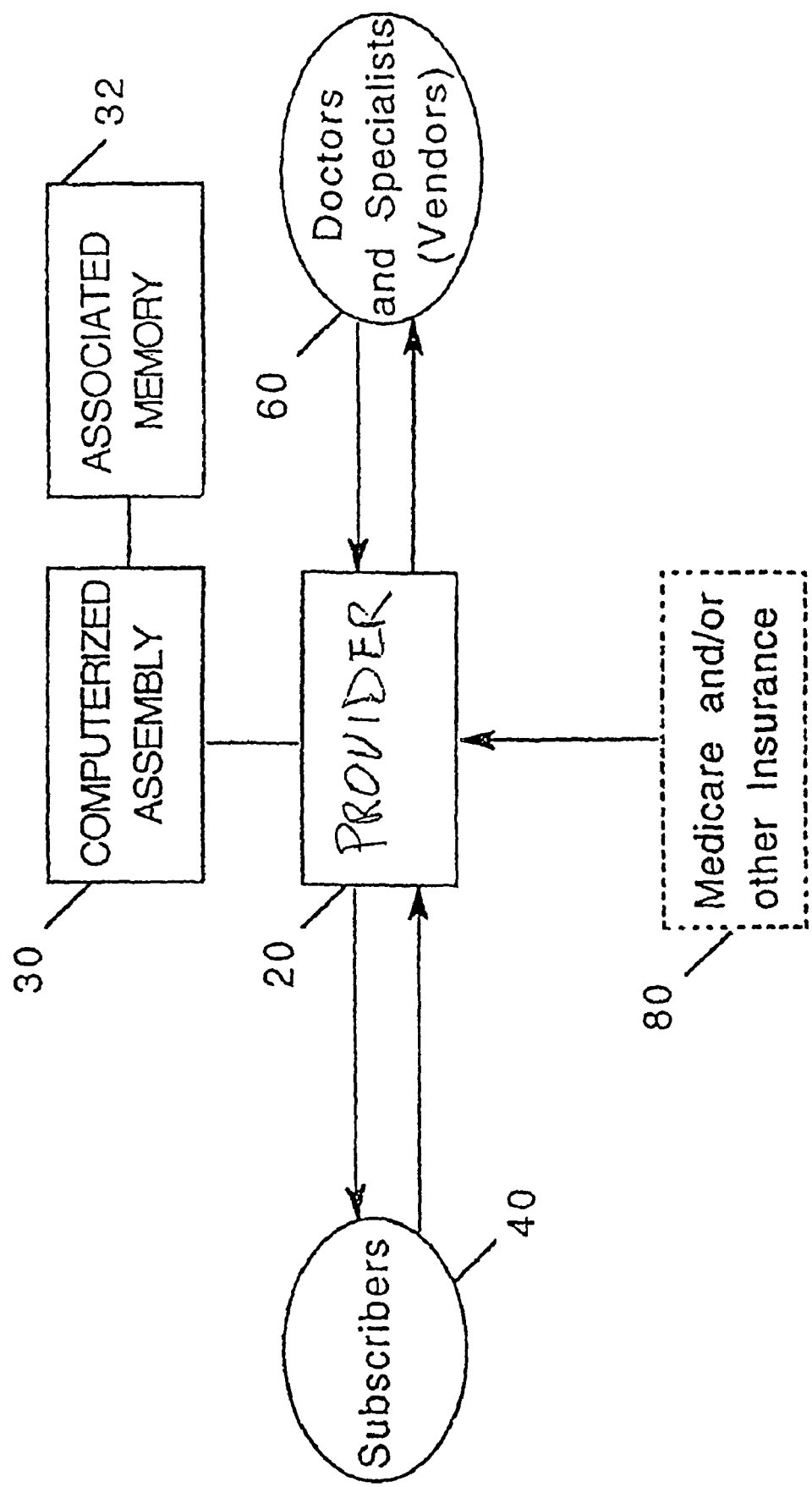
FIG. 1 is a schematic representation of a preferred embodiment of a health care delivery system and method of the present invention.

As shown in the accompanied drawings, the health care delivery system and method of the present invention comprises a plurality of subscribers 40, desirous of receiving health care services, entering into a contractual obligation with a provider or providing entity 20 responsible for the performance and administration of the health care delivery system and method of the present invention. As such, the providing entity 20 has access to and utilization of a processor and/or computerized assembly 30 with an appropriate data bank and associated memory 32 readily accessible for both the input and output of data as schematically indicated. In addition, the providing entity 20 may be associated with a plurality of vendors, normally comprising doctors or other health care professionals. These "outside" vendors are consulted in situations where a specialist and/or medical procedure is required for proper treatment of a subscriber 40, which may not be normally available on an "in-house" basis by the providing entity 20.

Figure 3:
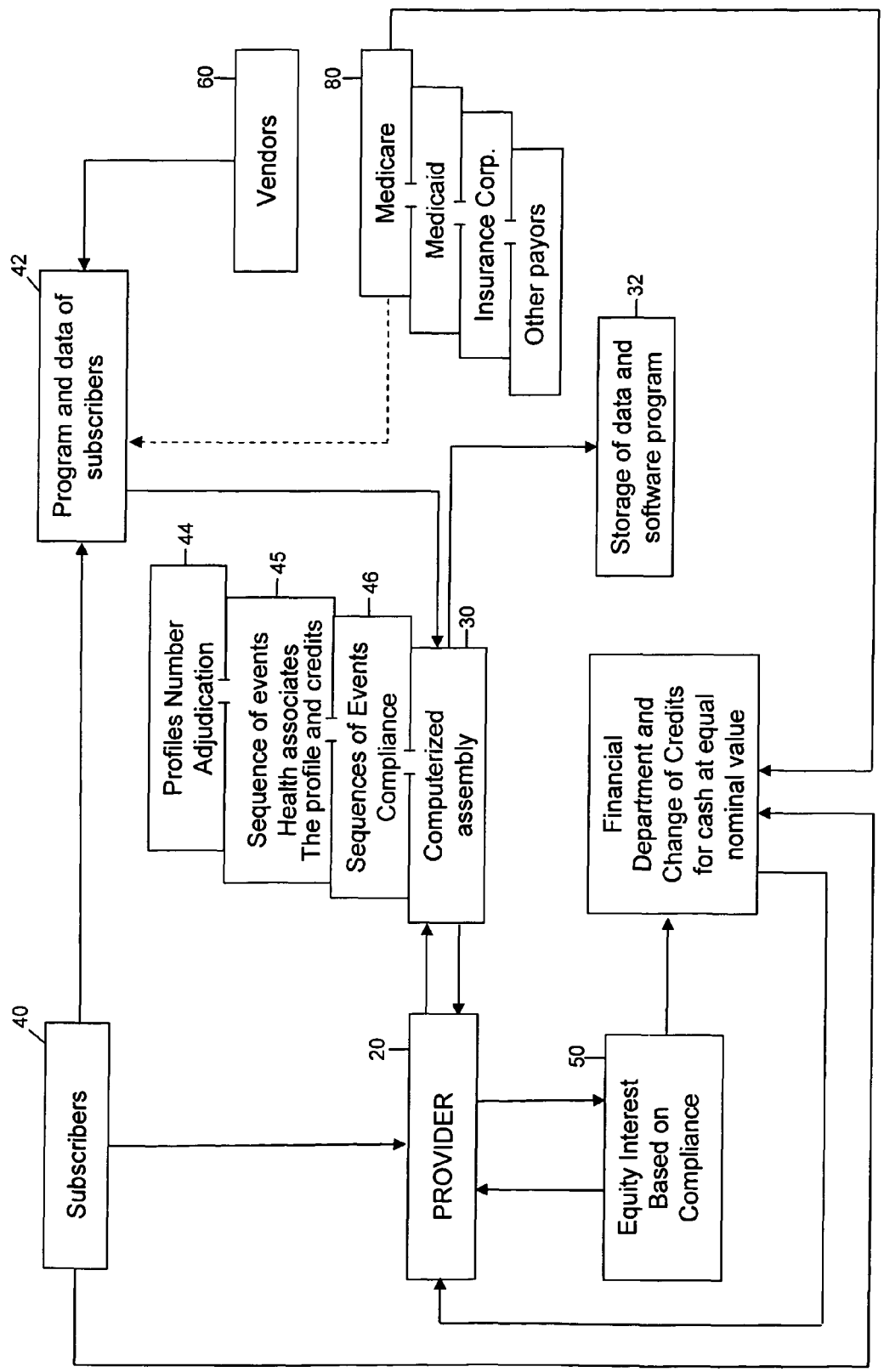
FIG. 3 is schematic representation of the preferred embodiment of the present invention disclosed in greater detail.

As will also be explained in greater detail hereinafter the health care delivery system and method of the present invention may involve payment for some or all of the medical care treatment, procedures, etc. by payors other than the individual subscribers 40. With reference to FIGS. 1 and 3, such additional or third-party payors may include conventional sources of health care funds such as Medicare, Medicaid, insurance corporations, and/or a variety of other payors generally indicated as 80.

Upon subscribing to the health care delivery system and method of the present invention, in direct association with a providing entity 20, each of the individual subscribers 40 provides personal particulars and/or characteristics which may include, but are not limited to gender, age, medical and clinical history, etc. In accordance with such personal particulars or characteristics as well as any current or existing medical condition which may require medical attention, the individual subscriber is categorized and assigned at least one of a plurality of predetermined health profiles 44. Each of the plurality of profiles 44 are predetermined and are either specifically or generally defined to include predetermined parameters of personal particulars and/or characteristics which include, but are not limited to, gender, age, medical history, etc. as set forth above. Storage of the plurality of profiles, as defined above, may be maintained within the database and/or software program facilities of the memory 32, as also set forth above.

The personal particulars and/or characteristics 42 used to categorize and/or assign the plurality of profiles 44 are important in the immediate establishing of one or more preventative treatment regimens that can be undertaken by the subscriber in order to minimize or prevent future maladies and/or for the eventual treatment, cure and/or medical procedures rendered to the individual subscribers when it is determined that medical care is necessary. More specifically, when medical attention or care is required to be administered to one of the subscribers, or preventative action is to be initiated, the subscriber's assigned profile 44 is retrieved from the appropriate data base and/or storage facilities 32 and reviewed along with the particular medical condition of the subscriber which requires treatment and/or which is sought to be prevented or minimized. In this regard, it is understood that for the purposes of the present invention, a medical treatment may include steps to cure, prevent, correct and/or minimize an existing condition, and/or preventative steps designated to prevent or minimize the occurrence or severity of a possible future condition. This future condition may include a condition determined as likely or possible based on a subscriber's current health state, age, family history, gender, exposure to other conditions, etc.

Figure 2:
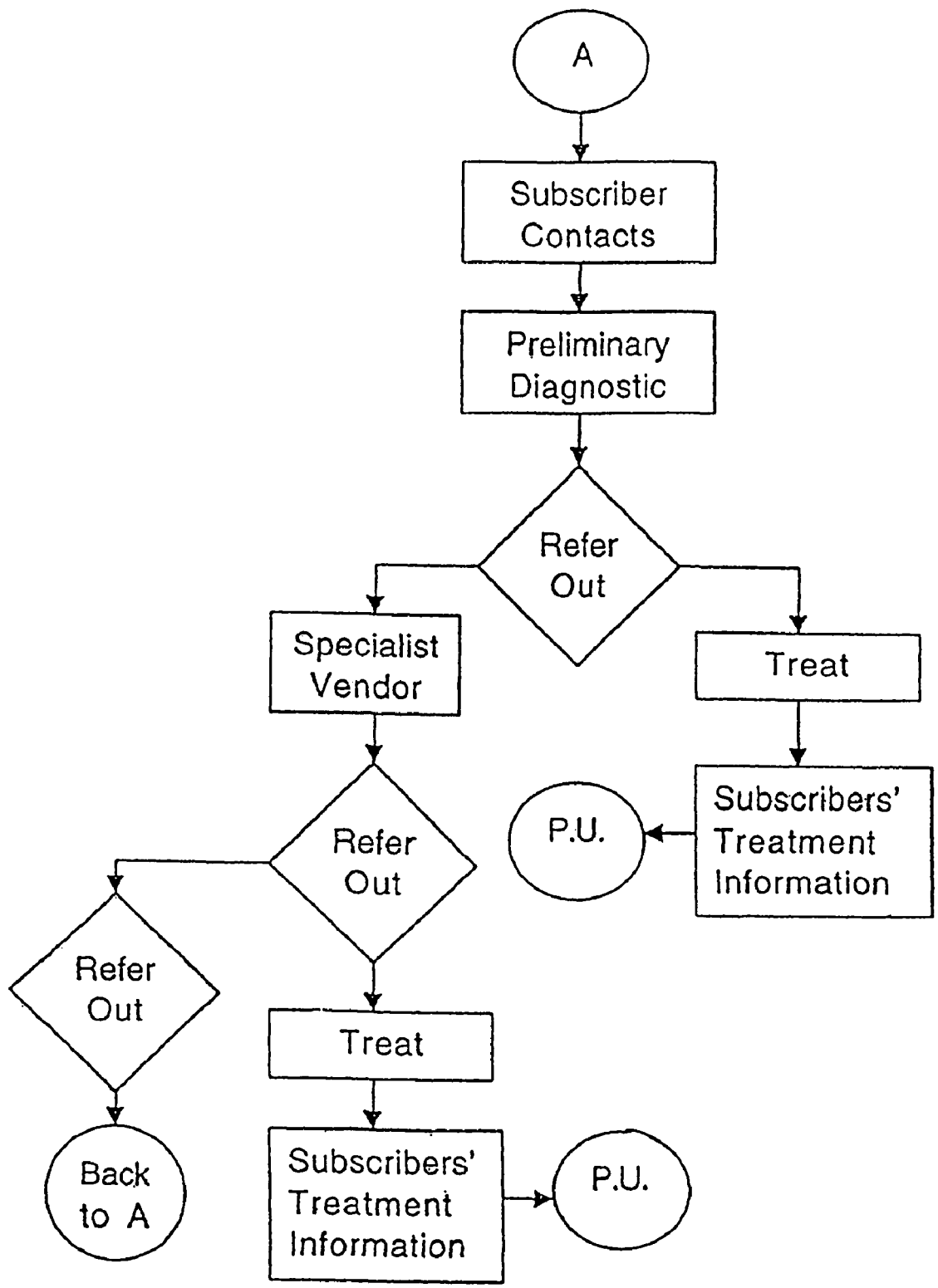
FIG. 2 is a schematic representation in the form of a flow chart disclosing the steps of administering the health services to subscribers.

As best shown in FIG. 2, when a subscriber 40 requires medical treatment or care, the providing entity 20 is contacted and the assigned or categorized profile 44 associated with an individual subscriber 40 is reviewed. Thereafter, preliminary diagnostic procedures are conducted and a method of treatment is established. Thereafter, the providing entity 20 determines an individualized health care program which incorporates a treatment regimen for addressing the medical condition of the subscriber 40.

Figure 2A:
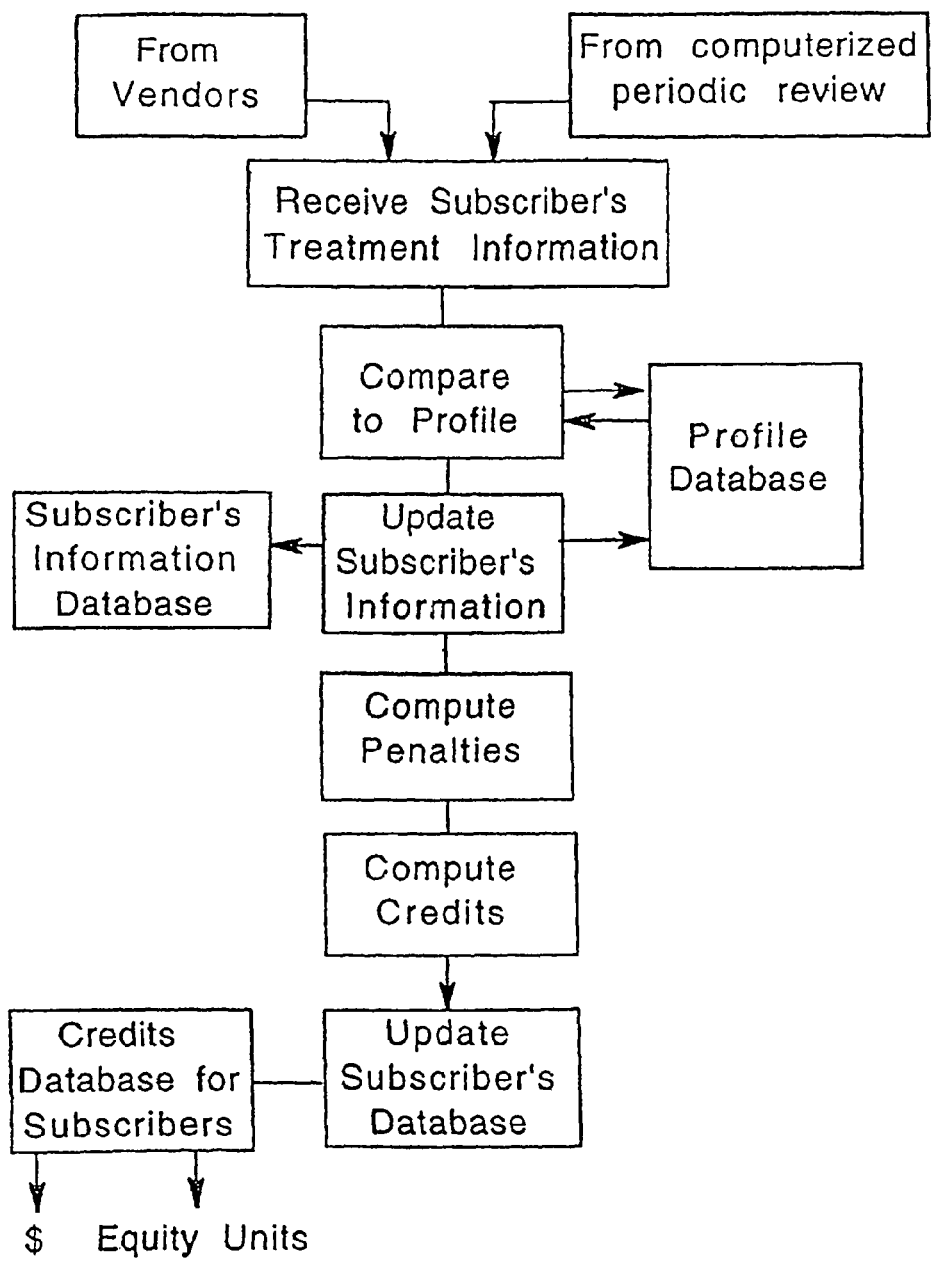
FIG. 2a is a flow chart disclosing operative features of a central processing unit included in the preferred embodiment of the present invention.

As schematically represented in FIGS. 1, 2 and 2A, the providing entity 20 also must determine whether treatment is to be preformed "in-house" or should best be referred to one or a plurality of health care specialists "vendor". Assuming the subscriber 40 is to be treated on an in-house basis, the aforementioned treatment regimen will involve specific subscriber's treatment information. The subscriber's treatment information outlines in detail the various treatment, procedures, medications, etc. required for the proper treatment of the individual medical condition for which the individual subscriber 40 requests health care. The subscriber's treatment information, as part of the individualized treatment regimen, will be delivered to the processing unit or facilities, which includes the computerized assembly and associated memory capabilities, 30, and or 32 for processing and administration, as represented in FIG. 1 and described in greater detail in FIG. 2A.

However, the prescribed treatment regimen of a given subscriber 40 may be referred out to a specialist vendor 60, already associated with the providing entity 20 as set forth above. The individual specialist and/or a variety of different health care professionals are consulted to assure that treatment can and will be preformed in accordance with the subscriber's treatment information or treatment regimen as dictated by the predetermined health care program, as set forth above. Again it is to be emphasized that the health care program which is determinative of and includes a treatment regimen comprising medication, exercise, outside activities, etc. and define what may referred to as a "sequence of events" 45 which must be preformed on or by the individual subscribers 40. In the context of FIGS. 2 and 3, such "sequence of events" 45 is to be included with and or used synonymously with the subscribers treatment information. As with an in-house treatment regimen described above, the "sequence of events" or subscribers treatment information is properly inputted into the processing facilities and/or storage, data base, etc. 30 and 32.

In order to accomplish a rapid and effective cure or otherwise perfect or maximize the benefit of a medical treatment, including preventative treatments, to an individual, the predetermined procedures or "sequence of events" 45 performed on or by the subscriber must be closely adhered to. Deviation from the sequence of events 45 of the prescribed treatment regimen may in fact delay or prevent cure of a medical condition or result in a worsening thereof dependant upon the degree of compliance, or may result in a failure to receive the benefit sought from a preventative plan. Therefore the health care delivery system and method of the present invention incorporates a motivational feature associated therewith. Such motivational feature comprises a detailed review, over a period of time, of the activities of the subscriber 40 at least to the extent of whether the subscriber has or is complying, as at 46, with the sequence of events 45 included in the subscriber's treatment information.

With reference to FIGS. 2A and 3, the compliance 46 of an individual subscriber 40 with the sequence of events 45 of the prescribed treatment regimen is determined, at least in part, from retrieving the stored data regarding the subscriber's activities. As indicated with reference to FIG. 2 the subscriber's performance is continuously updated by the vendors 60 or in-house personnel, dependent on those responsible for the subscriber's care. Such updated information is maintained in the computer, software and/or processor facilities 30 and 32 as part of the treatment information. Accordingly the providing entity has direct access to the compliance performance 46 with the prescribed sequence of events 45 required for medical care, treatment or cure or a diagnosed medical condition. Therefore, the input from the vendors 60 when the mode of treatment is referred out to health care specialists and/or from a computerized periodic review of the varied information inputted into the processing utilities 30 and/or 32 from in-house personnel serves to maintain a record of the performance (compliance or non-compliance) of an individual subscriber. Further, an individual subscriber's information is updated based upon both current and past activities relating to the prescribed sequence of events 45.

The motivational factors included in the health care delivery system and method of the present invention thereby includes an incentive system comprising the awarding of both "credits" and "penalties" based upon the subscriber being in compliance or non-compliance 46 with the aforementioned sequence of events 45 of the treatment regimen of the health care program assigned to an individual subscriber. Clearly, compliance of a subscriber with the prescribed sequence of events will result in the awarding of credits. To the contrary non-compliance with the sequence of events will result in the awarding of penalties. The motivational factor to demonstrate adequate compliance therefore comes into play when a sufficient amount of credits, in excess of penalties, have been awarded to a subscriber, which results in the granting of motivational awards to a subscriber 40 based on a collective consideration of the credits and penalties which have been awarded.

As schematically represented in FIGS. 2A and 3, the motivational awards, when the amount of credits awarded to a subscriber for compliance with the sequence of events is sufficient, may include valuable consideration including money and/or an equity interest 50 in a given entity, particularly an equity interest 50 in the providing entity 20. Moreover, the awarding of an equity interest 50 in the providing entity 20 is intended to be clearly distinguishable from the awarding of money and/or the accumulation of investment credits in one or more of various types of accounts. To the contrary, as used herein the granting of an equity interest 50 in an entity and in particular in the providing entity 20 is equivalent to ownership in that entity. As such the awarded equity interest may represent a reward of significantly greater and possibly increasing value, when considered from both a long term and short term basis, than an award of money, credits in an account, etc. Accordingly, regardless of the category or form of the motivational award, the granting thereof, either in the form of money, equity interest 50 in the providing entity 20 or other valuable consideration is processed by an appropriate financial department which is responsible for administering the financial services of the providing entity 20, as indicated.

It is again emphasized with respect to the prescribed sequence of events 45 of a treatment regimen, the deciding entity and/or authorized personal will take into consideration the personal particulars and/or characteristics defining a subscriber's profile, as well as the medical and clinical history, including specific medical or preventative conditions for which medical treatment is being rendered. Equitable considerations will of course have to be injected into the administration and determination of compliance with the sequence of events in accordance with philosophies of each providing entity 20.

Therefore, motivational features involved in the incentive system of the health care delivery system and method of the present invention will urge the individual subscribers to perform the various sequences of events of the treatment regimen and associated prescribed health care program assigned to an individual subscriber. However, in some cases of severe non-compliance, valuable consideration will not be awarded in any form.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A healthcare system comprising:

a computerized assembly comprising a computer processor and associated memory, said computerized assembly further comprising input and output means for communicating with one or more healthcare providers, said healthcare providers interacting personally with one or more individual healthcare program subscribers to provide healthcare services to said individual healthcare program subscribers, wherein each said individual healthcare program subscriber has his or her own individual personal health characteristics, and wherein said input and output means are used to receive from and provide to said one or more healthcare providers data pertaining to said individual personal health characteristics pertaining to each said individual healthcare program subscriber, one or more databases storing said individual personal health characteristics data of each of said individual healthcare program subscribers, one or more predetermined healthcare profiles and one or more treatment regimens being established based upon said one or more predetermined healthcare profiles, said one or more treatment regimens being assigned to a said individual healthcare program subscriber based upon categorization of said individual healthcare program subscriber into one or more of said healthcare profiles based upon said individual healthcare program subscriber's individual personal health characteristics, said one or more treatment regimens comprising a sequence of activities to be performed by said individual healthcare program subscriber and individualized to said individual healthcare program subscriber, and being administered by said one or more healthcare providers, said system receiving from said one or more healthcare providers data pertaining to said individual healthcare program subscriber's performance of said sequence of activities as said activities are performed by said individual healthcare program subscribers, said sequence of activities being designed to cure, prevent, minimize or treat an existing medical condition or prevent or minimize a future medical condition of said individual healthcare program subscriber, said healthcare system further comprising one or more software applications stored in said associated memory of said computerized assembly and run by said computer processor for categorizing said individual healthcare program subscribers into one or more of said predetermined healthcare profiles based on said individual healthcare program subscriber's personal health characteristics data, for establishing and assigning to said individual healthcare program subscriber one or more of said treatment regimens based upon one or more of said predetermined healthcare profiles which correspond to said individual healthcare program subscriber's individual personal health characteristics data, and for receiving from healthcare providers administering said assigned treatment regimen and actively monitoring said individual healthcare program subscriber's performance of said activities comprising said sequence of activities of said assigned treatment regimen data pertaining to said individual healthcare program subscriber's adherence to said assigned treatment regimen, said assignment of said one or more treatment regimens to said individual healthcare program subscriber being made without requiring said individual healthcare program subscriber to have a specific ailment requiring healthcare services, said health care system including an incentive system comprising one or more software applications stored in said associated memory of said computerized assembly and run by said computer processor for assigning credits to each said individual healthcare program subscriber dependent on said subscriber's degree of compliance with said assigned one or more treatment regimens, assigning penalties to each said individual healthcare program subscriber dependent on said subscriber's degree of noncompliance with said assigned one or more treatment regimens and for issuance of awards to each said individual healthcare program subscriber based on said individual healthcare program subscriber's balance of said credits and penalties.

2. A health care system as recited in claim 1 wherein said award comprises an equity interest in said providing entity.

3. A method of administering healthcare service, said method comprising:

providing a computerized assembly comprising a computer processor with a database and associated memory to implement a healthcare program to provide healthcare services to individual healthcare subscribers, said computerized assembly further comprising input and output means for communicating with one or more healthcare providers, said one or more healthcare providers interacting personally with said individual healthcare program subscriber to provide healthcare services to each said individual healthcare program subscriber, wherein each said individual healthcare program subscriber has his or her own individual personal health characteristics, receiving from and providing to said one or more healthcare providers via said input and output means data pertaining to said individual personal health characteristics pertaining to a said individual healthcare program subscriber, storing in a database a plurality of healthcare profiles for categorizing a said individual healthcare subscriber based upon said individual healthcare subscriber's individual health characteristics, and one or more treatment regimens established based upon said one or more healthcare profiles, said one or more treatment regimens comprising a sequence of activities which has been individualized to said individual healthcare system subscriber based on said individual healthcare program subscriber's individual personal health characteristics and to be performed by a said individual healthcare program subscriber, storing in a database one or more of said healthcare profiles selected from said plurality of healthcare profiles, said stored one or more healthcare profiles being assigned to a said individual healthcare program subscriber based on said individual healthcare program subscriber's individual personalized health characteristics, storing in a database one or more of said treatment regimens corresponding to said healthcare profile that is assigned to a said individual healthcare program subscriber, receiving from said healthcare providers compliance monitoring data pertaining to said individual healthcare program subscriber's performance of said sequence of activities comprising said treatment regimen as said healthcare program subscriber performs said activities, to determine whether said individual healthcare program subscriber is complying with said treatment regimen, implementing via one or more software applications stored in said associated memory of said computerized assembly a preventative care and healthcare cost reduction incentive system based on use of said stored compliance monitoring data to determine compliance or non-compliance by each said individual healthcare program subscriber with said individual healthcare program subscriber's assigned treatment regimen, assigning credits and penalties to each said individual healthcare program subscribers based on the degree of compliance or non-compliance by a said individual healthcare program subscriber with said treatment regimen assigned to said individual healthcare program subscriber, and issuing awards, based on a collective consideration of said credits and penalties, to those of said individual healthcare program subscribers having an excess of credits over penalties, wherein said credits are assigned to those of said individual subscribers evidencing compliance with the assigned treatment regimen, and wherein said penalties are assigned to those of said individual healthcare program subscribers evidencing non-compliance with the assigned treatment regimen.

4. A method as recited in claim 3 wherein said award comprises an equity interest in said providing entity.

5. A method as recited in claim 3, wherein said assignment of said one or more treatment regimens to said individual healthcare program subscribers is made without requiring said individual healthcare program subscribers to have a specific ailment requiring healthcare services.

6. A method as recited in claim 3, wherein said one or more treatment regimens are designed to cure, prevent, minimize or treat an existing medical condition or prevent or minimize a future medical condition.

7. A method as recited in claim 3, wherein said preventative care and healthcare cost reduction incentive system causes said individual healthcare program subscribers to have a financial and health motivation to comply with said assigned one or more treatment regimens.

8. A healthcare system providing financial incentives for preventative care, thereby reducing the long-term costs of healthcare, comprising:

a computerized assembly comprising a computer processor and associated memory, said computerized assembly further comprising input and output means for communicating with one or more healthcare providers, said healthcare providers interacting personally with one or more individual healthcare program subscribers to provide healthcare services to said individual healthcare program subscribers, wherein each said individual healthcare program subscriber has his or her own individual personal health characteristics, and wherein said input and output means are used to receive from and provide to said one or more healthcare providers data pertaining to said individual personal health characteristics of said individual healthcare program subscribers, one or more databases storing said individual personal health characteristics data of each of said individual healthcare program subscribers, one or more predetermined healthcare profiles and one or more preventative care treatment regimens corresponding to one or more of said one or more predetermined healthcare profiles, said one or more treatment regimens being assigned to a said individual healthcare program subscriber based upon categorization of said individual healthcare system subscriber's individual personal health characteristics, said one or more treatment regimens being administered by said one or more healthcare providers and comprising a sequence of activities to be performed by said individual healthcare program subscriber, said sequence of activities being designed to prevent or minimize a future medical condition of said individual healthcare program subscriber and data pertaining to said healthcare program subscribers' adherence to said one or more treatment regimens, said data being received from said one or more healthcare providers as said healthcare program subscriber performs said sequence of activities comprising said treatment regimen, said healthcare system further comprising one or more software applications stored in said associated memory of said computerized assembly and run by said computer processor for categorizing each said individual healthcare program subscriber into one or more of said predetermined healthcare profiles based on said individual healthcare system subscriber's personal health characteristics data, for establishing and assigning to each said individual healthcare program subscriber one or more of said treatment regimens corresponding to one or more of said predetermined healthcare profiles which correspond to said individual healthcare program subscriber's personal health characteristics data, and for receiving data pertaining to said individual healthcare program subscriber's performance of said sequence of activities comprising said treatment regimen, said healthcare system including an incentive system comprising one or more software applications stored in said associated memory of said computerized assembly and run by said computer processor for assigning credits and penalties to each said individual healthcare program subscribers dependent on said individual healthcare program subscriber's degree of compliance or non-compliance with a designated one of said treatment regimens and for issuance of an award for compliance with a designated one of said treatment regimens, said compliance being determined based on retrieval and review of said data received and stored in a said database regarding said individual healthcare program subscriber's performance of acts prescribed by said treatment regimen, by consideration of credits and penalties issued to said individual healthcare program subscriber when said data recorded in said database regarding said individual healthcare program subscriber's performance of acts prescribed by said treatment regimen indicates compliance with said treatment regimen, and issuance of penalties to said individual healthcare program subscriber when said data indicates noncompliance with said treatment regimen.

9. The healthcare system of claim 8, wherein said award comprises an equity interest in said providing entity.

* * * * *